US005643915A

United States Patent [19]

Andrulis, Jr. et al.

[11] Patent Number: 5,643,915
[45] Date of Patent: Jul. 1, 1997

[54] TREATMENT OF ISCHEMIA/REPERFUSION INJURY WITH THALIDOMIDE ALONE OR IN COMBINATION WITH OTHER THERAPIES

[75] Inventors: Peter J. Andrulis, Jr., Bethesda; Murray W. Drulak, Gaithersburg, both of Md.

[73] Assignee: Andrulis Pharmaceuticals Corp., Beltsville, Md.

[21] Appl. No.: 471,352

[22] Filed: Jun. 6, 1995

[51] Int. Cl.$^6$ .......................... A01N 43/42; A61K 31/44; A61K 31/445
[52] U.S. Cl. .......................... 514/279; 514/290; 514/291; 514/292; 514/323; 514/408; 514/410; 514/411; 514/422; 514/424; 514/425
[58] Field of Search .................................. 514/279, 290, 514/291, 292, 323, 408, 410, 411, 422, 424, 425

[56] References Cited

U.S. PATENT DOCUMENTS

| 5,434,170 | 7/1995 | Andrulis, Jr. ........................ 514/323 |
| 5,443,824 | 8/1995 | Piacquadio ........................ 424/78.02 |

*Primary Examiner*—Nathan M. Nutter
*Attorney, Agent, or Firm*—Isaac Angres

[57] ABSTRACT

In accordance with the present invention, a method is provided for treating reperfusion injury, ischemia and runaway inflammatory conditions with thalidomide alone or in combination with other drugs selected from the group consisting of nitrates, beta-adrenoceptor blocking agents, antiplatelet/thrombolytic drugs, drugs acting as the arachindonic acid cascade and calcium antagonists. Pharmaceutical compositions comprising thalidomide alone or in combination with other drugs are also provided.

20 Claims, No Drawings ns 5,643,915

TREATMENT OF ISCHEMIA/REPERFUSION INJURY WITH THALIDOMIDE ALONE OR IN COMBINATION WITH OTHER THERAPIES

FIELD OF THE INVENTION

The present invention generally relates to preventing or ameliorating tissue damage that occurs during ischemia/reperfusion conditions involving cytokine, growth factor and chemotactic cascades which arise during these severe inflammatory conditions. More particularly, the invention is related to the use of thalidomide as a therapeutic and/or protective agent in conditions characterized by ischemia/reperfusion such as acute myocardial infarction, stroke, spinal cord injury, head injury, severe infectious disease, inflammatory bowel conditions, cancer, and certain surgical procedures.

The present invention further relates more generally to the protection of or inhibition of damage to various types of tissue whenever the inflammatory condition involves the damaging effects of oxygen free radicals and oxygen intermediates, and cytokines and growth factors which are involved in "runaway" inflammatory conditions. Hence the invention also relates to methods of treating various tissue types from mammalian species against the damaging effects of singlet oxygen, hydroxyl radical, cytokines and growth factors using thalidomide.

The invention also relates to methods for improving post-ischemic myocardial and neuronal tissue functions in mammalian species by administering thalidomide and derivatives thereof.

In another aspect of the invention, thalidomide can be combined with thrombolytic agents, anti-coagulants, anti-sense nucleotides, steroidals, and other compounds, such as nitrates, beta-adrenoceptor blockers, anti-platelet drugs, drugs acting on the arachidonic acid cascade and calcium antagonists.

The present invention further relates to a novel method for treating ischemia/reperfusion injury including, but not limited, to that associated with coronary and cerebral occlusion with thalidomide, alone or in combination with other therapies which prevent, ameliorate, or treat such injury. The present invention also relates to methods of treating ischemia/reperfusion injury with multiple inhibitors to cytokine/growth factors such as TNF-alpha and IL-1-beta as well as pharmaceutical compositions containing relevant cytokine/growth factor inhibitors and/or ischemia/reperfusion injury therapies.

BACKGROUND OF THE INVENTION AND DESCRIPTION OF PRIOR ART

Tissue damage caused by the presence of cytokines and growth factors during severe inflammatory conditions (a.k.a. runaway inflammatory conditions) can result from blockage of blood flow due to stroke, myocardial infarction (ischemia) or surgical intervention, infectious diseases, parasitic and other inflammatory conditions. It is believed that cytokines are responsible for "communication" between cells which ultimately leads to gene activation. These discrete signaling molecules are considered benign to tissue in a healthy state. Cytokines include interleukins, various growth factors, interferons, and colony-stimulating factors. However, the net biological effect of the interaction of this class of molecules can also be inflammation and in this instance, cytokines are also known to play a major role in a wide variety of disease states such as cancer, allergy, infection, inflammation, angiogenesis, and differentiation. Cytokines and growth factors together are also believed to play a major role in restenosis (neointimal hyperplasia or proliferation following percutaneous transluminal coronary angioplasty and related procedures for removing blockages within blood vessels and lymph ducts).

The mechanism by which tissue is damage during a runaway inflammatory response caused, for example, by a bacterial infection is as follows: Inflammatory cytokines such as tumor necrosis factor and interleukin-1 activate intracellular, microbiocidal neutrophils. In their normal, defensive operation, neutrophils aggregate and release toxic granule proteins and the products of neutrophil oxidatively burst to destroy the harmful microbe. However, in a runaway process, the neutrophil aggregation and release of microbiocidal substances are not localized in the vicinity of the microbe, leading to damage of the host tissue. This chain of events occurs in a number of diseases associated with, e.g., infectious agents of the immune system, chronic inflammation, and the respiratory system, as well as during numerous surgical procedures.

Accordingly, it is a goal of the invention to use thalidomide to ameliorate tissue damaged by severe inflammatory responses, without interfering with host tissue defense mechanisms. In particular, the invention recognizes the great need for ameliorative drug therapies for stroke, heart attack, restenosis, adult respiratory distress syndrome (ARDS) and septic shock (the latter two conditions having a high likelihood of fatality), asthma, hearing loss associated with bacterial meningitis, inflammatory bowel conditions, and dozens of other conditions.

Blood flow reductions in the heart can result in dysfunction of this organ and cell death if the flow reduction is severe enough. Restoration of coronary blood flow early during a heart attack is becoming a clinical reality with the advent and improvements in thrombolytic, mechanical, and surgical interventions. While early restoration of blood flow by thrombolysis or following transient ischemia can prevent or mitigate the degree of cell death (infarction), reperfusion can still result in some degree of cardiac dysfunction or cell death (also referred to as stunned myocardia). Thus, it would be of great clinical value to find a means to preserve normal function of the heart during reperfusion and during various forms of cardiac surgery.

Oxygen free radicals and oxygen intermediates, especially singlet oxygen and the hydroxyl radical, cause extensive tissue damage. Free radicals and oxygen intermediates within living cells arise from endogenous sources, for example, from mitochondrial electron transport chain, oxidant enzymes, phagocytic cells and auto-oxidation reactions, as well as from exogenous sources such as cigarette smoke, "redox cycling" drugs and pesticides, heat stress, and ionizing radiation. These oxygen species damage compounds of all biochemical classes, including nucleic acids, protein and free amino acids, lipids and lipoproteins, carbohydrates, and connective tissue macromolecules. In addition, these oxygen species are believed to have an impact on cellular activities, such as membrane function, metabolism, and gene expression. Both singlet oxygen and hydroxyl radical are known to produce damaging strand breaks in DNA during reperfusion (specifically, during the reoxygenation aspect of reperfusion following ischemia) and during severe inflammatory conditions. Also, these oxidants, in the presence of metal ions (e.g., iron), initiate lipid peroxidation, which, in turn, produces mutagens, carcinogens, and other reactive oxygen species.

Numerous clinical conditions implicate oxygen radicals as the cause of tissue damage in single organs such as erythrocytes (e.g., lead poisoning), lungs (e.g., acute respiratory distress syndrome), heart and cardiovascular system (e.g., atherosclerosis), kidney (aminoglycoside nephrotoxicity), GI tract (e.g., free-fatty-acid-induced pancreatitis), brain and CNS (e.g., senile dementia, hypertensive cerebrovascular injury, and cerebral trauma), eye (e.g., cataractogenesis), and skin (e.g., solar radiation and contact dermatitis). Clinical conditions involving multiorgan disorders linked to oxygen radicals include, for example, inflammatory-immune injury, ischemia/reperfusion states, radiation injury, aging, cancer and amyloid diseases.

In spite of the more recently known deleterious effects of these oxygen species, the scientific community has focused its attention on the superoxide anion for the past two decades, leaving largely unexplored the role of singlet oxygen and the hydroxyl radical in human disease. Thus, no drugs that specifically target these oxygen species are currently available. It is one of the goals of the present invention to use a series of drugs that can inhibit the "runaway" inflammatory response in tissue experiencing oxidative stress. In particular, the need for such drugs is particularly great for protecting or treating cardiac tissue undergoing heart attack, angioplasty, and cardiac surgery. The invention also addresses the need for ameliorative drug therapies for ischemic stroke, vasospasm during subarachnoid hemorrhage, head injury, spinal cord injury, and neurosurgery, whereby the effects of damage from reperfusion and inflammation would be prevented or lessened.

Additionally, heart disease is the biggest cause of death in the Western world. There are many different forms of heart disease and disease states that can develop from a number of different factors including stress, diet, tobacco use, and genetic make up of the individual. Ischemia is a heart disease condition characterized as a local hypoxia caused by mechanical obstruction or occlusion of the blood supply. Oxygen radicals have been implicated as important mediators of tissue injury during myocardial ischemia and reperfusion. A number of studies have shown that free radicals, particularly superoxide anions ($O_2^-$) and hydroxyl radicals are generated following reperfusion of the ischemic myocardium and have linked the free radical generation to the loss of contractile function. Superoxide artion is relatively unreactive and is considered dangerous because its dismutation results in the formation of hydrogen peroxide which can potentially generate the highly reactive hydroxyl radical (OH) in the presence of transition metal ions. It is therefore generally believed that ultimate tissue damage occurs due to OH radicals. Indirect proof for the involvement of OH radicals in ischemia/reperfusion injury is derived from observations of a protective effect of OH radical scavengers such as dimethylthiourea (DMTU), dimethylsulfoxide, and mannitol. In addition, certain agents which prevent the formation of hydroxyl radicals have also demonstrated a protective effect, including deferoxamine, superoxide dismutase, and catalase.

Another active oxygen species is singlet molecular oxygen ($^1O_2$). Singlet oxygen is not a radical; rather, it is an electronically excited state of oxygen which results from the promotion of an electron to higher energy orbitals. In Kukreja et al., *Biochim. Biophys. A*, 990:198–205 (1990); the Kukreja et al., *Am. J. Physiol.*, 259:H1330–H1336 (1989), data was presented which demonstrated that superoxide anion or hydrogen peroxide are the least reactive species in damaging sarcolemma or sarcoplasmic reticulum. Therefore, it might be inferred that the only species believed to be injurious in myocardial tissue is the OH radical that can initiate lipid peroxidation which can in turn, produce lipid free radicals that may become important sources of singlet oxygen in vivo. Hence, the damage often attributed to the OH radical could be the resultant effects of other intermediate reaction products including lipid free radicals and singlet oxygen.

Janero et al., *J. Mol. Cell Cardiol.*, 21:1111–1124 (1989), showed that alpha-tocopherol provides cellular protection by acting as a chain breaker in the lipid peroxidation process, not by scavenging the $O_2$—radical per se. Singlet oxygen is also acted upon by alpha-tocopherol. Hearse et al., *Circ. Res.*, 65:146–153 (1989), and Vandeplassche et al., *J. Mol. Cell Cardiol.*, 22:287–301 (1990) (abstract) showed that $^1O_2$ generated from exogenous sources is able to mimic ischemia/reperfusion-induced myocardial damage. Tarr et al., *J. Mol. Cell Cardiol.*, 21:539–543 (1989), recently reported that rose bengal, when applied extracellularly to frog atrial myocytes, induced a prolongation followed by a reduction of action potential duration. In addition, Donck et al., *J. Mol. Cell Cardiol.*, 20:811–823 (1988) reported that isolate myocytes exposed to rose bengal light rapidly experience ultrastructural injury.

In Kukreja et al., *Abs. of 63rd Sci. Sess.* (AHA) (Dallas), 1068 (1990), it was reported that singlet oxygen generated from photosensitization of rose bengal induced significant inhibition of calcium uptake and $Ca^{2+}$-ATPase activity in isolate sarcoplasmic reticulum. This damage caused by singlet oxygen could be significantly reduced using L-histidine, but not with SOD or catalase. Misra et al., *J. Biol. Chem.*, 265:15371–15374 (1990), reported that L-histidine is a scavenger of singlet oxygen. In contrast, SOD and catalase are scavengers of superoxide anion. Kim et al., *Am. J. Physiol.*, 252:H252–H257 (1987), demonstrated that L-histidine provides significant protection of sarcolemmal $Na^+K^+$-ATPase activity following ischemia/ reperfusion in guinea pig hearts.

As explained above, ischemia is a decreased blood supply to a body part or organ which is often marked by pain and organ dysfunction. Ischemic tissues become hypoxic and in some extreme cases anoxic. Pathologic processes due to ischemia such as heart disease and strokes are the first and third leading causes of death in the United States respectively. However, a substantial proportion of tissue injury that accompanies ischemia is not directly due to the lack of oxygen getting to tissues but rather occurs during reperfusion which is when oxygen is reintroduced into the tissues (McCord, *N. E. J. M.*, 312:159–163, 1985). During reperfusion there is a conversion of oxygen into superoxide and secondarily-derived oxygen radicals which trigger a series of events that culminate in massive tissue damage (Granger et al., *Covan. Physiol. Bhaum*, 71:67–75, 1981; Roy et al., In; Greenwald, R., Cohen. G. Eds., Oxyradicals and their Scavenger systems, Vol. 2., Cellular and Molecular Aspects, New York; Elsevier Science, 1983; pages 154–157; Parks, *Gastroenterology*, 82:9–15, 1982). The pathway by which superoxide is produced is catalyzed by the enzyme xanthine oxidase which is derived during ischemia from xanthine dehydrogenase. Xanthine dehydrogenase is widely distributed among tissues. It converts rapidly to xanthine oxidase as a result for proteolysis and sulfhydryl oxidation (Batelli et al., *Biochem. J.*, 126:747–749, 1972; Della Corte, *Biochem. J.* 126:739–745, 1972). There appears to be a correlation between xanthine dehydrogenase levels in tissue and their susceptibility to ischemia/reperfusion injury, with organs such as the intestines, heart and lungs that have high xanthine dehydrogenase levels being more susceptible to injury while skeletal muscle which has low levels of xanthine dehydrogenase being relatively resistant to such injury (McCord, *N. E. J. M.*, 312:159–163 (1985).

McCord, *N. E. J. M.*, 312:159–163 (1985), hypothesized that xanthine dehydrogenase is converted to xanthine oxidase when blood flow to a tissue is decreased to the point where availability of oxygen limits ATP production. This results in a drop in cellular energy levels and the $Ca^{2+}$ ion gradient across cellular membranes can no longer be maintained. An elevated cytosolic $Ca^{2+}$ concentration occurs which in turn activates a protease that converts xanthine dehydrogenase to xanthine oxidase. Concurrently, depletion of cellular ATP during ischemia results in an elevated AMP concentration. Such AMP is catabolized to hypoxanthine which upon reperfusion, reacts with oxygen in a chemical reaction catalyzed by the newly formed xanthine oxidase yielding oxygen radicals as an end product.

It should be emphasized at this point that even though generation of superoxide and other oxygen-derived radicals lead to tissue damage, reperfusion of ischemic tissues itself results in very little damage (Korthuis et al., *Am. J. Physiol.*, 256:11315, 1989; Perry et al., *Am. J. Physiol.*, 254:6366, 1988). Zimmerman and Granger, *Surg. Clin. North America*, 72:(1)65–83 (1992) determined that these oxidants mediate microvascular permeability, which develops after one hour of reperfusion, and lesions are produced by three hours during ischemia/reperfusion. They hypothesized that xanthine oxidase-derived oxidants were produced in epithelial and endothelial cells. Such oxidants mediate production and release of pro-inflammatory cytokines which attract, activate and promote adherence of neutrophils to microvascular endothelium. These neutrophils are believed to be the primary mediator of reperfusion injury (Granger, *Amer. J. Physiol.*, 255:H 1269–H 1275, 1988). A number of studies using in vitro models of ischemia/reperfusion injury have supported this contention. For example, exposure of endothelial cells to anoxia-reoxygenation resulted in increased intracellular levels of xanthine oxidase, increased generation of oxygen derived radicals, cell dysfunction and death. Inhibitors of xanthine oxidase prevented production of oxygen derived radicals and cellular damage (Zweier et al., *Proc. Natl. Acad. Sci.* (U.S.A.), 85:4045–4050, 1988; Ratych et al., *Surgery*, 102:122–131, 1987; Inauen et al., *Free Radical Biol. Med.*, 9:219–23, 1990b). Neutrophils added to anoxic and reperfused endothelial cells adhered significantly to these cells and this adherence was markedly reduced by superoxide dismutase which suggested that the superoxide radical mediates anoxia/reperfusion-induced neutrophil adhesion to endothelial cells (Suzuki et al., *Am. J. Physiol.*, 257:H1740–1745, 1989; Yoshida et al., *Am. J. Physiol.* 262:H1891–H1898, 1992). Oxygen radicals such as superoxide stimulate endothelial cells to produce inflammatory cytokines such as platelet activating factor (PAF) and leukotriene $B_4$ ($LTB_4$) (Granger and Kvietys, *Can. J. Physiol. Pharmaceutical*, 71:67–75, 1993; Zimmerman and Granger, *Surg. Clin. North Amer.*, 72:(1)65–83, 1992). Mangino et al., *Amer. J. Physiol.*, 257:6299 (1989) detected a 687% increase in mucosal $LTB_4$ levels in the dog ileum model during reperfusion, but no increase was initially seen during ischemia. Zimmerman et al., *Gastroenterology*, 99:1358–1363 (1990) saw a 200% increase in $LTB_4$ after reperfusion of the cat intestine. This group further demonstrated that reperfusion-induced neutrophil infiltration was significantly reduced in animals pretreated with lipooxygenase inhibitor or a $LTB_4$ receptor antagonist which indicates that $LTB_4$ mediates reperfusion-induced neutrophil infiltration into the surrounding tissue. It has also been demonstrated that a PAF receptor antagonist and catalase ameliorated the adhesion-promoting ability of supernatants from reperfused endothelial cells (Yoshida et al., *Amer. J. Physiol.*, 262:H1891–H1898, 1992). A PAF receptor antagonist L659, 989 also was shown to prevent hypoxia-induced neutrophil adhesion to human umbilical vein endothelial cells (Milhoan et al., *Amer. J. Physiol.*, 256:H956–H962, 1992). DuBois et al., *J. Immunol.*, 143:964–70 (1989) reported that PAF mediates TNF-alpha generation in alveolar macrophages through endogenous $LTB_4$ production. TNF-alpha, in turn, is capable of inducing release of large amounts of PAF, as seen in rat peritoneal macrophage leading DuBois et al. to hypothesized that $LTB_4$ or PAF antagonists may prove to be effective therapeutics to block reperfusion-induced inflammation.

Another pro-inflammatory cytokine, IL-1 beta, has been demonstrated to play a causal role in ischemia/reperfusion injury of the canine gracilis muscle (Ascer, *Amer. Vas. Surg.*, 6:69–73, 1992) and in cerebral ischemia in rats (Minami et al., *J. Neurol.*, 58:390–392, 1992). Neutrophil accumulation seen in rat heart ischemia/reperfusion injury was shown to be IL-1 beta-dependent (Brown et al., *Proc. Natl. Acad. Sci.* (U.S.A.), 87:5926–30, 1990). Similar to TNF-alpha, IL-1 beta production was enhanced by $LTB_4$ (Rola-Pleszczynski and Lemaire, *J. Immunol*, 135:3958, 1985). TNF-alpha and IL-1 beta have been shown to be involved in neutrophil-mediated inflammatory damage at a number of levels. TNF-alpha and IL-1 beta produced by macrophages induces significant increases in E-selectin receptor expression on endothelial cells within two hours. Such E-selectin expression enhanced the ability of endothelial cells to initially trap and bind neutrophils at a body site where injury is occurring. By 24 hours, however, expression of E-selectin on endothelial cells begins to wane and is replaced by increased expression of ICAM-1 which is also stimulated by TNF-alpha and IL-1 beta (Lipsky, *Springer Semin. Immunopathol*, 11:123–162, 1989). The neutrophils initially bound to E-selectin then bind to ICAM-1. Such binding of neutrophils to ICAM-1 is an important step towards diapedesis of neutrophils which must happen before neutrophil-mediated reperfusion injury can occur. TNF-alpha also upregulates CD 11/CD 18 receptors on neutrophils which are responsible for binding to the previously described ICAM-1 endothelial cell receptors (Gamble et al., *Proc. Natl. Acad. Sci.* (U.S.A.), 82:8667, 1985).

Seekamp et al., *Amer. J. Pathol.*, 143:(2)453–63 (1993) showed that in a rat hind-limb ischemia model where TNF-alpha and IL-1 beta plasma levels increased significantly within one hour of reperfusion, polyclonal antibody to TNF-alpha and IL-1 beta conferred significant protection from vascular injury in both lung and muscle. Similar results were also obtained using soluble TNF-alpha receptor and IL-1 receptor antagonist. E-selectin expression in lung vasculature was blocked when animals were treated with anti-TNF-alpha antibodies. This work indicates that therapeutic strategies which inhibit TNF-alpha and IL1 beta production may be effective in limiting reperfusion-based tissue damage. It has already been demonstrated that thalidomide inhibits TNF-alpha production in erythema nodosum leprosum patients (Sarno et al., *Clin. Exp. Immunol*, 84:103–108, 1991) and in vitro in monocytes (Sampaio et al., *J. Exp. Med.*, 173:699–703, 1991) while Shannon et al., *American Society Microbiology Annual Meeting-Abstract U-53* (1990) indicated that thalidomide inhibited IL-1 beta production in vitro. It is the purpose of this invention, therefore, to use thalidomide to inhibit ischemia/reperfusion-based inflammatory damage from occurring by administering thalidomide alone or in combination with other anti-ischemia/ reperfusion and antiinflammatory therapeutics including, but not limited, to other inhibitors of cytokines such as TNF-alpha, IL-1 beta, PAF and/or $LTB_4$ Such other current anti-ischemia/reperfusion injury therapeutics include:

Nitrates

This group of therapeutics is especially characterized by three compounds in common use today, glyceryl trinitrate, isosorbide dinitrate and isosorbide 5 mononitrate. There is a problem of tolerance and attenuation of responses to nitrates (Parker et al., Europ., Heart J., 10: (Suppl A) 1-55, 1989, Flaherty, Drugs, 37:523-50, 1989).

Beta-Adrenoceptor Blocking Agents

This group of therapeutics includes Labetalol (2-hydroxy-5-[1-hydroxy-2-[(1methyl-3 phenylpropyl amino]ethyl] benzamide), Arotinolol (±-5-[2-[[3-(1,1-dimethylethyl)-amino]-2-hydroxypropyl]thio]-4-thiazolyl]-2thiophenecarboxamide), Carvedilol (1-(9H-carbozol-4-yloxy)-3-[[2-(2-methoxyphenyl)ethyl]amino]-2propanol), Celiprolol(N'-[3acetyl-4-[3-(1,1-dimethylethyl)-amino]-2-hydroxypropoxy]phenyl]-N,N-diethylurea), Dilevalol ([R-(R*R*)]-2 hydroxy-5-[1-hydroxy-2-[(1 methyl-3-phenylpropyl) amino]ethyl]benzamide), Niprodolol(3,4-dihydro-8-[2-hydroxy-3-(1-methylethyl) amino]-2H-1-benzopyran-3-ol 3nitrate), and Tertalolol ((±)-1-[3,4-dihydro -2H-1-benzothio-pyran-8-yl)oxy]-3-(1,1-dimethylethyl)amino]-2-propanol). The side effects associated with these agents are bronchospasms, heart failure and cold extremities.

Anti-Platelet/Thrombolytic Drugs and Drugs Acting on the Arachidonic Acid Cascade This group includes all drugs that effect platelet-blood vessel wall interactions by preventing platelet aggregation and thrombus formation such as, but not limited to, ticlopidine (5-[2-chlorophenyl)methyl]-4, 5, 6, 7 -tetrahydrothieno[3,2-c]pyridine), aspirin (acetyl salicylic acid), streptokinase (streptococcal fibrinolysin) and tissue plasminogen activator (TPA) also known as fibrinokinase. Drugs acting on the arachidonic acid cascade include inhibitors of cyclo-oxygenase and/or lipooxygenase such as Indomethacin (1-(4-chlorobenzoyl)-5-methoxy-2-methyl-1H -indole-3-acetic acid), Aspirin, and BW 755C as well as more selective inhibitors such as, but not limited to, compounds increasing the synthesis, release or inhibiting the degradation of prostacyclin ((5Z, 9α, 11α, 13E, 15 S)-6,9-epoxy-11,15-dihydroxyprosta-5, 13-dien-1-oic acid) or other longer lasting synthetic derivatives of prostacyclin such as iloprost, inhibitors of thromboxane A2 synthetase, and drugs blocking thromboxane A2 receptors such as ONO-3708 ([1S-[1 α,2β(Z), 3 α(S*),5α]]-7-[3-(Cyclopentylhydroxy-acetal)amino]-6,6-dimethylbicyclo [3.1.1]hept-2-yl]-5-heptenoic acid), AH-19437([1α(Z),2β, 5α]-(±)-7-[2-(4-Morpholinyl)-3-oxo-5-(phenyl-methoxy) cyclopentyl]-5-heptenoic acid methyl ester) BM-13177([p-[2-(Benzenesulfonamido)ethyl]phenoxy]acetic acid), AH-23848, BM-13505 ([p-[2-chlorobenzene sulfonamido) ethyl]phenoxy]-acetic acid), SQ-28668([1α,2α(Z),3α(1E, 3S*,4R*),4α]- 7-[3-(3-Hydroxy-4-phenyl-1-pentenyl)-7-oxabicyclo[2.2.1 ]hept-2-yl]-5-heptenoic acid), GR-32191 (±)-(Z)-7-[(1R,2R,3S,5S)-3-Hydroxy-5-[(p-phenylbenzyl) oxy]-2-piperidinocyclopentyl]-4-heptenoic acid), and EP-045.

A recent finding that indicates platelet aggregation mediated by thromboxane A2 occurs during coronary thrombolysis limits the effectiveness of such therapy alone and points to the necessity of combination therapy with thromboxane synthetase inhibitors or receptor antagonists with thrombolytic agents (Fitzgerald et al., 1989). The efficacy of this group of drugs overall though remains under debate (Massingham and John, 1990).

Calcium Antagonists

This group consists of the following subclasses of drugs:

a) Calcium Entry Blockers

This includes compounds such as 1,4-dihydropyridines, benzothiazepines and phenylalkylamines. The 1,4-dihydropyridines, however, elicit marked peripheral vasodilatation resulting in reflex tachycardia. This causes blood flow to be directed away from the ischemic tissue thereby increasing the potential of subsequent tissue damage. Calcium entry blockers in general are poor calcium overload blockers (Van Zwieten, 1986) and are less than optimal anti-ischemia drugs.

b) Calcium Overload Blockers

This includes diphenylalkylamines such as flunarizine ((E)-1-[Bis(4-fluorophenyl)methyl]-4-(3-phenyl-2 propenyl)piperazine), lidoflazine (4-[4,4-Bis(4-fluorophenyl)butyl]-N-(2,6-dimethylphenyl)-1-piperazineacetamide), miofiazine and cinnarizine(1-(Diphenylmethyl)-4-(3-phenyl-2-propenyl)piperazine). phenyl -2-propenyl) piperazine).

c) Intracellular Calcium Antagonists

This includes bepridil(Beta-[2-methylpropoxy)methyl]-N-phenyl-N-(phenylmethyl)-1-pyrrolidineethanamine), CERM 11956, dopropidil, KT-362, HA-1004 and HA-1077.

d) Directly Acting Cytoprotectants

An example of this group is ranolazine((±)-N-Dimethylphenyl)-4-[2-hydroxy-3-(2-methoxyphenoxy) propyl]-1-piperazineacetamide).

e) Bradycardic Agents

This includes falipamil, AQ-AH-208 and UL-FS-49.

f) Calmodulin Antagonists

This group includes fendiline (gamma-phenyl-N-(1-phenylethyl)benzene-propanamine), SIM 6080 and CGS 93438.

Thalidomide was first synthesized and marketed in the 1950's as a sedative. The toxicity of the compound was so low that a dose killing 50% of animals ($LD_{50}$) could not be established. Thalidomide was therefore thought to be a safer alternative to barbiturates. In 1961 thalidomide administered to pregnant women resulted in an epidemic of congenital malformations. The incidence of malformed babies paralleled the sales of thalidomide and quickly dropped off when thalidomide was removed from the market.

Oral administration of thalidomide in the range of 100-200 mg in adult humans resulted in a peak blood level of 0.9-1.5 rag/liter after 4-6 hours. Hydrolyric cleavage of thalidomide occurs in vitro, the rate of which increases as the pH increases. However, hydrolytic cleavage of thalidomide in serum is much slower than in vitro at pH 7.4. This may be due to thalidomide being highly bound to plasma proteins. Studies in animals demonstrated high thalidomide concentrations in the gastrointestinal tract, liver and kidneys with lower concentrations in the muscle, brain and adipose tissue. In pregnant animals, thalidomide can pass across the placenta.

Although a complete study of thalidomide metabolism in humans has not been performed, in animals the main pathway for thalidomide breakdown appears to be nonenzymatic hydrolytic cleavage. Even though immunodulatory effects of thalidomide have not been clearly defined at the molecular level, thalidomide has been used to treat a number of immunologically-based diseases such as aphthous ulcers (Jenkins et al., *Lancet*, 2: 1424–6, 1984; Grinspan, *J. Amer. Acad. Dermatol*, 12: 85–90, 1985; Revuz et al., *Arch. Dermatol*, 126:923–7, 1990), Graft vs Host Disease (Lim et al., *Lancet*, 1:117, 1988; McCarthy et al. *Lancet*, 2:1135, 1988; Henley et al., *Lancet*, 2:1317, 1988), erythema nodosum leprosum (Sheskin, *Lepr. Rev*, 36:183–7, 1965; Sheskin and Convit, Int. J. Lepr., 37:135–46, 1969; Pearson and Vedagiri, *Lepr. Ar.*, 40:111–6, 1969), Behcets Syndrome (Saylan and Saltik, *Arch. Dermatol*, 188:536, 1982; Jorizzo et al., *Arch. Int. Med.*, 146:878–81, 1986), actinic prurigo (Londono, *Int. J. Dermatol.*, 12:326–8, 1973; Lowell et al., *Brit. J. Dermatol*, 108:467–71, 1983), ulceralive colitis (Waters et al., *Brit. Med. J.*, 1:792, 1979) and discold lupus erythematosus Knop et al., Arch Dermatol Res., 271:165–70, 1981). In these studies dosages of thalidomide ranging from 100 mg/day to 800 mg/day were administered without serious side effects.

SUMMARY OF THE INVENTION

The primary objective of the present invention is to provide a method of treatment for ischemia/reperfusion injury with inhibitors of cytokine and/or growth factors.

A further objective of the present invention is the treatment of ischemia/reperfusion injury with thalidomide alone or in combination with other agents that inhibit cytokines and/or growth factors and/or classes of therapeutics used to treat this condition.

Another objective of this current invention is to provide a method for treating ischemia/reperfusion injury with thalidomide at a given regimen.

An additional objective of the current invention is to provide compositions of matter comprising inhibitors of cytokine and/or growth factors with agents of other classes of ischemia/reperfusion injury therapeutics.

A still further objective of the present invention is a method for the therapeutic treatment of ischemia/ reperfusion injury which comprises treatment with thalidomide and other drugs on different days, by diverse schedules.

It is thereof an object of this invention to provide a method of using thalidomide alone and with other agents in the treatment of schemia/reperfusion injury that occurs in many diverse clinical situations.

It is also an object of this invention to use thalidomide to indirectly protect the ultrastructure of cardiac cells.

Another object of the invention is to control (e.g., prevent or ameliorate) tissue damage caused by severe runaway inflammatory responses by administering thalidomide.

An example of applicant's invention using thalidomide alone or in combination with other anti-inflammatory and/or anti-ischemia/reperfusion therapies, is when thalidomide is given with pentoxifylline and a glucocorticoid, such as dexamethasone. The activity of each of these agents would be expected to enhance that of the other two in inhibiting TNF-alpha synthesis since each of these agents acts as an inhibitor at a different point in this synthesis. Pentoxifylline inhibits TNF-alpha gene transcription (Doherty et al., 1991), while thalidomide enhances TNF-alpha m-RNA degradation (Moreira et al., 1993) and glucocorticoids such as dexamethasone inhibit TNF-alpha m-RNA translation (Han et al., 1990).

DESCRIPTION OF THE PREFERRED EMBODIMENTS

The present invention is directed to a method for the prevention and treatment of ischemia/reperfusion injury in a mammal, which comprises administering to said afflicted mammal a therapeutically effective amount of thalidomide.

Additionally, the instant invention is also directed to a method for the treatment and prevention of ischemia/ reperfusion injury in a mammal which comprises administering to said afflicted mammal a therapeutically-effective amount of thalidomide in combination with other drugs effective in the treatment of ischemia/reperfusion injury selected from the group consisting of nitrates, beta-adrenoceptor blocking agents, antiplatelet drugs, thrombolytic agents, drugs acting as the arachidonic acid cascade and calcium antagonists.

The invention is also directed to a method for the prevention and treatment of runaway inflammation conditions induced by cytokines and growth factors in a mammal which comprises administering to said mammal a therapeutically-effective amount of thalidomide and derivatives thereof.

The present invention further provides a method for inhibiting physiological damage induced by free radicals in mammal, said method comprising administering to said mammal a therapeutically-effective amount of thalidomide.

The therapeutically-effective amounts of thalidomide are typically 30 mg to 1500 mg and preferably 200 mg to 500 mg. When thalidomide is used in combination with other drugs effective in the treatment of reperfusion injury, the amount of thalidomide is typically in the range of about 30 mg to about 1000 mg while the other drugs present in the range of about 10 mg to 500 mg. For example, an effective combination for treating reperfusion injury a gelatin capsule containing 200 mg of thalidomide and 60 mg of labetalol given three times daily. Two capsules each containing the active ingredient may also be prescribed.

The precise amount of thalidomide alone or with the other active materials mentioned above will vary depending, for example, on the condition for which the drug is administered and the size and kind of the mammal. Generally speaking, the thalidomide can be employed in any amount of effective in the treatment of reperfusion injury, ischemia, and runaway inflammatory conditions. The symptoms of the above conditions generally are improved.

For humans, typical effective amounts of thalidomide for use in the unit dose compositions of the present invention range from about 30 mg to 1500 mg per 24 hours; however, greater amounts may be employed, if desired. This range is based on administration to a 70 kg human. A preferred amount is 200 mg to 500 mg. The more preferred range contains about 200 mg to 500 mg of thalidomide per 24 hours.

As mentioned above, thalidomide may be given alone or in combination with other drugs which are also useful in the treatment of ischemia/reperfusion injury and runaway inflammatory conditions. For example, when thalidomide is used with a beta-adrenoceptor blocking agent such as labetalol, a typical formulation contains from about 100 mg to 500 mg of thalidomide and from about 50 mg to 150 mg of labetalol. The formulations are administered over a 24 hour period. The preferred drugs that can be combined with thalidomide are selected from the group consisting of nitrates, beta-adrenoceptor blocking agents, anti-platelet/ thrombolytic drugs, drugs acting on the arachidonic acid cascade and calcium antagonists.

The preferred nitrates are selected from the group consisting of glyceryl trinitrate, isosorbide dinitrate and isosorbide 5 mononitrate.

When thalidomide is combined with the beta-adrenoceptor blocking agents, said blocking agents are selected from the group consisting of labetalol, arotinolol, carvedilol, celiprolol, dilevalol, niprodolol and tertalolol.

The preferred anti-platelet/thrombolytic drug is selected from the group consisting of ticlopidine, aspirin, streptokinase and tissue plasminogen activator (TPA).

The drugs acting on the arachidonic acid cascade and selected from the group consisting of aspirin, indomethacin, prostacyelins, inhibitors of thromboxane A2 synthetase and thromboxane A2 receptor blockers.

The calcium antagonists are selected from the group consisting of 1,4-dihydropyridines, benzothiazepines, phenylalkylamines, flunarizine, lidoflazine, mioflazine (4-[4,4-Bis(p-fluoro-phenyl)butyl]-3-carbamoyl-2',6'-dichloro-1-piperazineacetanilide),cinnorizine, bepridol, CERM 11956 (N-1,3-Benzodioxol-5yl-β[(2-methylpropoxy) methyl-N-(phenylmethyl)-1-pyrrolidineethanamine), dopropidil(1-[1-(Isobutoxymethyl)-2-[[1-(1-propynyl) cyclo-hexyl]-oxy]-ethyl]-pyrrolidine), KT-362 (5-[N-(3,4-Dimethoxyphenethyl)-β-alanyl]-2,3,4,5-tetrahydro-1,5-benzothiazepine), HA 1004(N-(2-Guanidinoethyl)-5-isoquinoline-sulfonamide), HA 1077 (Hexahydro-1-(5-isoquinolinylsulfonyl)-1H-1,4-diazepine), ranolazine, falipamil (2-[3-[(3,4-dimethoxy phenethyl)methylamino] propyl]-5,6-dimethoxyphthalimidine), AQL 208 ((−)-1,2,3,4-Tetrahydro-1-(3,4,5-trimethoxy-benzyl)-6,7-isoquinolinediol), UL-FS 49 (3-[3-[(3,4-Dimethoxy phenethyl)methylamino]-propyl]-1,3,4,5-tetrahydro-7,8-dimethoxy-2H-3-benzazepin-2-one), Fendiline, SIM 6080 and C6S 93438.

The compound of the present invention can be prepared and administered in a wide variety of oral and parenteral dosage forms. It will be obvious to those skilled in the art that the following dosage forms may comprise as the active component, either thalidomide alone or in combination with other compounds.

Preferably the compounds of the present invention are administered orally, intramuscularly, subcutaneously or intravenously. For preparing pharmaceutical compositions from the compounds of the present invention, pharmaceutically-acceptable carders can be either solid or liquid. Solid form preparations include powders, tablets, pills, capsules, cachets, suppositories, and dispersible granules. A solid carder can be one or more substances which may also act as diluents, flavoring agents, solubilizers, lubricants, suspending agents, binders, preservatives, tablet disintegrating agents, or an encapsulating material.

In powders, the carder is a finely divided solid which is in a mixture with the finely divided active component. In tablets, the active component is mixed with the carder having the necessary binding properties in suitable proportions and compacted in the shape and size desired.

The powders, capsules and tablets preferably contain from five or ten to about seventy percent of the active compound. Suitable carders are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carder providing a capsule in which the active component, with or without other carders, is surrounded by a carder, which is thus in association with it.

Similarly, cachets and lozenges are included. Tablets, powders, capsules, pills, cachets, and lozenges can be used as solid dosages forms suitable for oral administration. For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool and thereby to solidify.

Liquid form preparation include solutions, suspensions, and emulsions, for example, water or water propylene glycol solutions. For parenteral injection, liquid preparations can be formulated in solution in aqueous polyethylene glycol solution.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparation which are intended to be converted, shortly before use, to liquid form preparation for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

It is also possible to administer thalidomide in a time-release formulation. A wide variety of methods are now available in the art for preparing time-release or long-acting compositions. Any of these time-release or long-acting formulations are suitable in the practice of the present invention as long as it does not adversely affect the effectiveness of the thalidomide in the treatment of reperfusion injury. Advantages of time-release formulations include a lower concentration of peak serum absorption which substantially reduces the adverse side effects and toxicity of the compound administered. In addition, a reduced frequency of administration results, which substantially improves patient compliance. A frequency of administration of every 12 or 24 hours would be preferred. In addition, more constant serum concentration of thalidomide would result thereby allowing a more consistent relief of symptoms.

The following examples, not to be construed as limiting, illustrate formulations which can be made according to the invention.

EXAMPLE 1

500 mg of thalidomide are mixed with 100 mg of aspirin. The active ingredients are triturated and q.s. with lactose to selected capsules size.

EXAMPLE 2

200 mg of thalidomide are mixed wit 100 mg of indomethacin. The active ingredients are triturated and q.s. with lactose to selected capsule size.

EXAMPLE 3

250 mg of thalidomide are mixed with 20 mg of labetalol. The active ingredients are triturated and q.s. with lactose to selected capsule size.

The following examples further illustrate the usefulness of the invention.

EXAMPLE 4

Hard gelatin capsules are prepared using the following ingredients

|  | Quantity (mg/capsule) |
| --- | --- |
| Thalidomide | 250 |
| Starch dried | 200 |
| Magnesium stearate | 10 |

The above ingredients are mixed and filled into hard gelatin capsules in 460 mg quantities.

EXAMPLE 5

|  | Quantity (mg/capsule) |
| --- | --- |
| Thalidomide | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 6

Tablets each containing 60 mg of active ingredients are made up as follows:

| Thalidomide | 60 mg |
| --- | --- |
| Starch | 45 mg |
| Microcrystalline cellulose | 35 mg |
| Polyvinylpyrrolidone (as 10% solution in water) Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing are compressed by a tablet machine to yield tablets each weighing 150 mg.

EXAMPLE 7

Capsules each containing 80 mg of medicament are made as follows:

| Thalidomide | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 8

Suspensions each containing 50 mg of medicament per 5 ml dose are made as follows:

| Thalidomide | 50 mg |
| --- | --- |
| Sodium carboxymethylcellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is added to produce the required volume.

EXAMPLE 9

Capsules each containing 150 mg of medicament are made as follows:

| Thalidomide | 150 mg |
| --- | --- |
| Starch | 164 mg |
| Microcrystalline cellulose | 164 mg |
| Magnesium stearate | 22 mg |
| Total | 500 mg |

The active ingredient, cellulose, starch and magnesium stearate are blended, passed through a No. 45 mesh U.S. sieve, and filled into hard gelatin capsules in 500 mg quantities.

EXAMPLE 10

250 mg of thalidomide are mixed with 5 mg of glycyl trinitrate. The active ingredients are triturated and q.s. with lactose to selected capsule sizes.

EXAMPLE 11

500 mg of thalidomide are mixed with 50 mg of tilopidone. The active ingredients are triturated and q.s. with lactose to selected capsule sizes.

EXAMPLE 12

250 mg of thalidomide are mixed with 60 mg of flunarize. The active ingredients are triturated and q.s. with lactose to selected capsule sizes.

Thalidomide according to the invention is effective in the protection of cells and vessels and tissue of various mammalian organs, inclusive of erythrocytes, lungs, heart and cardiovascular system, kidneys, gastrointestinal tract, brain, eye and skin against ischemia/reperfusion injury. In most, if not all, of these organs the tissue damage is the result of inflammation which occurs as a result of ischemia and/or reperfusion.

The thalidomide of the present invention is particularly useful for inhibiting and/or treating the following conditions: cardiac, cerebral, pulmonary and other ischemia; reperfusion injury; atherosclerotic disease; ultrastructural damage; and ARDS.

In another important aspect of the invention, the thalidomide of the present invention can be used in combination with plasminogen activators such as streptokinase, urokinase and tissue plasminogen activator (tPA), as well as related fibrinolytics, such as acylated plasminogen streptokinase activator complex, prourokinase, single chain urokinase, antibody-bound plasminogen activators and hybrid t-PA-urokinase proteins and other so called "third generation" thrombolytics.

Additionally, the thalidomide of the present invention can be used in combination with thrombolytics, adhesion antibodies, anti-platelet agents, direct anti-thrombins, antisense nucleotides, other antioxidants, and other biologically active ingredients. The combination of the thalidomide of the present invention with one or more of the above compounds may further reduce the damage to jeopardized tissue during reperfusion and during the severe inflammatory response by cells.

The formulations, could, for example, contain 50,000 to 50,000,000 IU/ml of tPA and 50 to 500 mg of thalidomide in a physiologically acceptable formulation. When SOD is used with the thalidomide of the present invention, its concentration could be in the range of 2,000 to 100,000 IU/ml.

PHARMACOLOGICAL TESTING PROTOCOLS

In vitro studies of the effect of thalidomide on macrophage functions in human cells In order to determine the ability of the thalidomide to reduce the severity of inflammatory responses, such as that seen in ischemia/reperfusion injury, in vitro studies of the following cell-damaging macrophage functions are measured as follows:

In vitro effect of thalidomide in human peripheral monocytes and whole blood stimulated by a concentration of 100 ng/ml of lipopolysaccharide (LPS), with incubation for 16 hours:

Tumor necrosis factor alpha (TNF-alpha) release
Interleukin-1 beta (IL-1 beta) release
Interleukin-1 beta receptor antagonist (IL-1 beta ra)
Interleukin-6
Interleukin-8
Granulocyte-macrophage colony-stimulating factor release (GM-CSF)
Procoagulant (tissue) function
Proliferation antibody assays (T-cell functions):
  OKT-3 (CD-3)
  phytohemagglutinin (PHA)
  mixed lymphocyte reaction (MLR)
Platelet derived growth factor (PDGF)
Oxidation burst from singlet oxygen ($^1O_2$) and hydroxyl radical (OH)
Adhesion
Superoxide radical In vitro effect of thalidomide in human peripheral monocytes and whole blood stimulated by a concentration of 200 mg/ml of Zymosan, with incubation for nineteen (19) minutes:

Platelet activating factor (PAF)
Prostaglandin ($PGE_2$)
Leukotriene ($LTB_4$)

In vitro effect of thalidomide in human peripheral monocytes and whole blood stimulated by a concentration of $5\times10^{-9}$ molar f-Met-Leu-Phe, with incubation for 90 minutes:

Slice Studies:

Electrophysiological responses to transient hypoxia are studied in neocortical brain slices from adult rats. Evoked responses and direct current (DC) potentials are recorded in layer III of the parietal cortex under normoxic and hypoxic conditions. The recovery of the evoked synaptic responses and DC potentials are measured for control and thalidomide treated slices. Adult Sprague-Dawley rats weighing 150–200 g are anesthetized with ether and sacrificed by decapitation. The basic procedures for preparing cortical brain slices are similar to those described previously for rat cortex. Briefly, the brains are rapidly removed and placed in cold, artificial cerebrospinal fluid (ACSF). The ACSF consists of following (in mM): 110.2 NaCl, 2.9 KCl, 1.1 $KH_2PO_4$, 2.1 $MgSO_4$, 1.8 $CaCl_2$, 22.8 $NaHCO_3$, 8.9 glucose. Using a razor blade, the brains are first hemisected at the midline, and then one of the hemispheres is bisected in a horizontal plane followed by a sagittal section. The superior-lateral quadrant of this dissection is placed on a tissue chopper and brain slices are cut in a coronal plane at a thickness of 400 mm. Brains slices containing the parietal cortex at the level of the striatum are placed in a petri dish containing ACSF. Slices are then transferred to a holding chamber held at 35.5° C. and maintained at interface with a humidified atmosphere of 95% $O_2$ 5% $CO_2$ (i.e. normoxic conditions). After a postsacrifice period of at least one hour, slices are transferred to a recording chamber as required.

A bipolar simulating electrode is positioned under visual guidance near the layer IV-layer V border in the slice. A glass microelectrode filled with 3M NaCl (1–5 megohm) is placed in layer III above the position of the simulating electrode. Stimuli are delivered once every fifteen seconds and the amplitude of evoked cortical potentials measured in response to a range of stimulation intensities. During the course of an experiment stimuli are administered at an intensity adjusted to elicit a response of approximately 60% of the miximal amplitude. Hypoxic conditions are achieved by substituting 99% $N_2$ for the normal 95% $O_2$ 5% $CO_2$ in the atmosphere of the recording chamber. The standard temperature in the recording chamber is 35.5° C.

A stable baseline of evoked responses is established under normoxic conditions for at least 15 minutes. Thalidomide (10 or 100 mM) or standard ACSF is the perfused for the remainder of the experiment. After 15 minutes of perfusion with thalidomide, hypoxic conditions are initiated. Hypoxic conditions were maintained until 10 minutes following the occurrence of hypoxic depolarization after which the slices are reoxygenated. Slices are monitored continuously for one hour following reoxygenation.

The potential neuroprotective effect of thalidomide is determined by comparing the recovery of evoked responses following hypoxia in control and thalidomide treated slices.

MCA Studies:

The experimental approach for focal cerebral ischemia entails reversible occlusion of both carotid arteries and singlet middle cerebral artery (MCA) for a period of three hours. This procedure produces consistent and substantial infarction of the rat neocortex ipsilateral to the MCA occlusion. This surgical procedure is in accordance with the guidelines of the National Institutes of Health. The postsurgery survival period is three days. Animals are sacrificed by decapitation under deep anesthesia. The endpoints of these studies are: a) volume of tissue infarction and, b) amount of edema. The volume of tissue infarction is determined by computerized morphometric analysis of TTC-positive and TTC-negative staining in serial, voronal sections of brain. The amount of edema is determined by comparing total neocortical volume in the infarcted and non-infarcted hemispheres of the brain.

Composition of groups:

Each experimental group includes 10 animals. A total of 60 animals are examined (i.e., 6 groups of 10 animals). The following groups will be examined.

| Groups | INJECTION TIMES (relative to ischemia) | | |
|---|---|---|---|
|  | 30 min pre | 30 min post | 3 hr post |
| 1) MCA only | − | − | − |
| 2) MCA + vehicle | − | + | + |
| 3) MCA + vehicle | + | + | + |
| 4) MCA + low dose thalidomide | − | + | + |
| 5) MCA + low dose thalidomide | + | + | + |
| 6) MCA + high dose thalidomide | − | + | + |
| 7) MCA + high dose thalidomide | + | + | + |

Species:
Sprague Dawley Rat (280–320 g)
Drug administration:
Injections are administered i.v.
Sacrifice:
3 days postsurgery
Analyses:
All sections are coded and the identity of the animal is unknown to the microscopist at the time of analysis. Computer-assisted morphometic analyses are performed to determined the volume of infarction and edema.

CLINICAL APPLICATIONS OF THE INVENTION

For treating a patient with a coronary artery thrombi, reconstitute 75 mg of urokinase (Abbokinase, Abbott Laboratories, North Chicago, Ill.) in 15.6 ml of sterile water. The urokinase solution is infused into the artery at a rate of 0.4 ml per minute for periods up to 2 hours. At the same time, the patient is treated with thalidomide (500 mg). To determine response to the therapy, periodic angiography is performed.

A test is performed to demonstrate combination therapy of superoxide dismutase (SOD) with thalidomide for protection of ischemic myocardium from reperfusion injury associated with oxygen radicals.

Under general anesthesia (sodium thiopental 25 mg/kg), animals are intubated and ventilated with 70% oxygen at a rate of 12 breaths per minute. A satisfactory level of anesthesia is maintained with intermittent boluses of pentothal as required. After skin preparation, a left anterior thoracotomy is performed, the pericardium incised and the heart exposed. The left anterior descending coronary artery is identified, isolated and encircled with a snare 1 cm from its origin. Temporary left anterior descending coronary artery occlusion it accomplished by tightening the snare and continues for 90 minutes. During the procedure, the heart rate and blood pressure are monitored utilizing a Hewlett-Packard 7758B 8-channel recorder. Arterial blood pressure is monitored through an 18 guage indwelling catheter in the right femoral artery and measured with a Hewlett-Parckard quartz transducer. Electrocardiographic evidence for anteroseptal myocardial ischemia is also monitored. Reperfusion of the ligated vessel after 90 minutes of ischemia is achieved by a gradual release of the snare to prevent the hyperemic response. A defibrillator is available in the room as are all necessary cardiotonic drugs in the event of cardiac fibrillation or circulatory collapse due to the left anterior descending coronary artery ligation. Therapeutic agents are infused in conjunction with reperfusion as follows: bovine superoxide dismutase with approximately 3000 units of activity per milligram assayed by the method of McCord, *J. Biol. Chem.*, Vol. 244, p. 6049 (1969) is obtained from Sigma Chemical Company, St. Louis, Mo. It is dissolved in 100 ml of normal saline and infused intravenously over 90 minutes starting 15 minute before restoration of perfusion. This stimulates the effects which occur during lysis of a coronary thrombus.

Thalidomide suspension is administered simultaneously with agents infused intravenously utilizing an IVAC 560 infusion pump. Infusion begins 15 minutes prior to release of the snare and continues until the total dose for each group has been administered. The chest is closed in layers. A chest tube is utilized to evacuate the pneumothorax and is removed when spontaneous respirations resume. Intravenous fluids are given (Lactated Ringer's Solution) to compensate for the 24 hour NPO period preceding the operation, in addition to a 3 to 1 ratio to compensate for blood loss. The animals are then maintained and followed closely for the next 24 hours. Each animal is then returned to the operating suite and under general anesthesia the previous incision is reopened. The animal is sacrificed utilizing a barbiturate overdose. The heart and proximal 4 cm of ascending aorta is excised being sure the include the origins of the coronary arteries.

All groups are subjected to the same procedure for identification of the area of the myocardium at risk for infarction and the area actually infarcted.

This technique involves perfusion of the left anterior descending coronary artery with 2,3,5-triphenyltetrazolium chloride, which stains the intact myocardium red and leaves the infarcted myocardium unstained. The limits of the area of myocardium at risk are determined by perfusing the remainder of the coronary system, via the aortic root, with Evans Blue dye. The area at risk is defined by a lack of Evans Blue stain.

It is not to be understood that the forms of the invention herein are to be taken as preferred examples of the same, and that various changes may be made without departing from the spirit for the invention or scope of the subjoined claims.

What is claimed is:

1. A method for the prevention and treatment of ischemia/reperfusion injury in a mammal which comprises administering to said afflicted mammal a therapeutically-effective amount of thalidomide.

2. The method of claim 1 further including one or more additional therapeutic drug effective in the treatment of ischemia/reperfusion injury wherein said one or more thereapeutic drug is selected from the group consisting of nitrates, beta-adrenoceptor blocking agents, anti-platelet/thrombolytic drugs, drugs acting on the arachidonic acid cascade and calcium antagonists.

3. The method of claim 2 wherein said nitrate is selected from the group consisting of glyceryl trinitrate, isosorbide dinitrate and isosorbide 5 mononitrate.

4. The method of claim 2 wherein said beta-adrenoceptor blocking agent is selected from the group consisting of 2-hydroxy-5-[1-hydroxy-2-[(1 methyl-3 phenylpropyl amino]ethyl]benzamide, (±)-5-[2-[[3-(1,1-dimethylethyl)-amino]-2-hydroxypropyl]thio]-4-thiazolyl]-2thiophenecarboxamide, 1-(9H-carbozol-4-yloxy)-3-[[2-(2-methoxyphenoxy)ethyl]amino]-2-propanol, N'-[3acetyl-4-[3-(1,1-dimethylethyl)-amino]-2-hydroxypropoxy]phenyl]-N,N-diethylurea, [R-(R*R*)]-2 hydroxy-5-[1-hydroxy-2-[(1 methyl-3-phenylpropyl)amino]ethyl]benzamide, 3,4-dihydro-8-2-hydroxy-3-(1-methylethyl)amino]-2H-1-benzopyran-3-ol 3 nitrate, (±)-1-[3,4-dihydro -2H-1-benzothio-pyran-8-yl)oxy]-3-(1,1-dimethylethyl)amino]-2-propanol.

5. The method of claim 2 wherein said anti-platelet/thrombolytic drug is selected from the group consisting of 5-[2-chlorophenyl)methyl-4, 5, 6, 7-tetrahydrothieno[3,2-c] pyridine, acetylsalicylic acid, streptococcal fibrinolysin, and fibrinokinase.

6. The method of claim 2 wherein said drug acting on the arachidonic acid cascade is selected from the group consisting of 1-(4-chlorobenzoyl)-5-methoxy-2-methyl-1H-indole-3-acetic acid, acetylsalicylic acid, (5Z, 9α, 11α, 13E, 15S)-6,9-epoxy-11,15-dihydroxyprosta-5,13-dien-1-oic acid, [1S-[1α,2β(Z), 3α(S*),5α]]-7-[3-(Cyclopentylhydroxy-acetal)amino]-6,6-dimethylbicylco[3.1.1]hept-2-yl]-5-heptenoic acid, [1α(Z),2β,5α]-(+)-7-[2-(4-Morpholinyl)-3-oxo-5-(phenyl-methoxy)cyclopentyl]-5-heptenoic acid methyl ester, [p-[2-(Benzenesulfonamido)ethyl]phenoxy] acetic acid, [p-[2-chlorobenzene sulfonamido)ethyl] phenoxy]-acetic acid, [1α,2α(Z), 3α(1E,3S*, 4R*), 4α]-7-[3-(3-Hydroxy-4-phenyl-1-pentenyl)-7-oxabicyclo[2.2.1] hept-2-yl]-5-hepten-oic acid and (+)-(Z)-7-[(1R,2R,3S,5S)-3-Hydroxy-5-[(p-phenylbenzyl)oxy]-2-pipiperidino cyclopentyl]-4-heptenoic acid.

7. The method of claim 2 wherein said calcium antagonists are selected from the group consisting of 1,4-dihydropyridines, benzothiazepines, phenylalkylamine, (E)-1-[Bis(4-fluorophenyl)methyl]-4-(3-phenyl-2 propenyl) piperazine, 4-[4,4-Bis(4-fluorophenyl)butyl]-N-(2,6-dimethylphenyl)-1-piperazine-acetamide, 1-(Diphenylmethyl)-4-(3-phenyl-2-propenyl)piperazine, Beta-[2-methylpropoxy)methyl]-N-phenyl-N-(phenylmethyl)-1-pyrrolidineethanamine, (±)-N-Dimethylphenyl)-4-[2-hydroxy-3-(2-methoxyphenoxy) propyl]-1-piperazineacetamide, gamma-phenyl-N-(1-phenylethyl)benzene-propanamine, 4-[4,4-Bis(p-fluoro phenyl)butyl]-3-carbamoyl-2',6'-dichloro-1-piperazineacetanilide, 1-[1-(Isobutoxymethyl)-2-[[1-(1-propynyl)cyclo-hexyl]oxy]ethyl]pyrrolidine, N-1,3-Benzodioxol-5yl-β[(2-methyl propoxy)methyl-N-(phenylmethyl)-1-pyrrolidineethanamine, N-(2-Guanidinoethyl)-5-isoquinoline-sulfonamide, Hexahydro-1-(5-isoquinolinylsulfonyl)-1H-1,4-diazepine, 2-[3-[(3,4-dimethoxy phenethyl)methylamino]propyl]-5,6-dimethoxyphthalimidine, (−)-1,2,3,4-Tetrahydro-1-(3,4,5-trimethoxy-benzyl)-6,7-isoquinolinediol, 3-[3[-(3,4-Dimethoxy phenethyl)methylamino]-propyl]-1,3,4,5-tetrahydro-7,8-dimethoxy-2H-3-benzazepin-2-one, 5-[N-(3, 4-Dimethoxyphenethyl)-β-alanyl]-2,3,4,5-tetrahydro-1,5-benzothiazepine.

8. A method for the prevention and treatment of runaway inflammatory conditions induced by cytokines and/or growth factors in a mammal which comprises administering to said mammal a therapeutically-effective amount of thalidomide.

9. The method of claim 8 further including an additional therapeutic drug effective in the treatment of runaway inflammatory conditions selected from the group consisting of nitrates, beta-adrenoceptor blocking agents, anti-platelet/thrombolytic drugs, drugs acting on the arachidonic acid cascade and calcium antagonists.

10. The method of claim 9 wherein said nitrate is selected from the group consisting of glyceryl trinitrate, isosorbide dinitrate and isosorbide 5 mononitrate.

11. The method of claim 9 wherein said beta-adrenoceptor blocking agent is selected from the group consisting of 2-hydroxy-5-[1-hydroxy-2-[(1 methyl-3 phenylpropyl amino]ethyl]benzamide, (±)-5-[2-[[3-(1,1-dimethylethyl)-amino-2-hydroxypropyl]thio]-4-thiazolyl]-2thiophenecarboxamide, 1-(9H-carbozol-4-yloxy)-3-[[2-(2-methoxyphenoxy)ethyl]amino]-2 propanol, N'-[3 acetyl-4-[3-(1,1-dimethylethyl)-amino]-2-hydroxypropoxy]phenyl]-N,N-diethylurea, [R-(R*R*)]-2 hydroxy-5-[1-hydroxy-2-[(1 methyl-3-phenylpropyl)amino]ethyl]benzamide, 3,4-dihydro-8-[2-hydroxy-3-(1-methylethyl)amino]-2H-1-benzopyran-3-ol 3 nitrate, (±)-1-[3,4-dihydro-2H-1-benzothio-pyran-8-yl)oxy]-3-(1,1-dimethylethyl)amino]-2propanol.

12. The method of claim 9 wherein said anti-platelet/thrombolytic drug is selected from the group consisting of 5-[2-chlorophenyl)methyl]-4,5,6,7-tetrahydrothieno[3,2-c] pyridine, acetylsalicylic acid, streptococcal fibrinolysin, and fibrinokinase.

13. The method of claim 9 wherein said drug acting on the arachidonic acid cascade is selected from the group consisting of 1-(4-chlorobenzoyl)-5-methoxy-2-methyl-1H-indole-3-acetic acid, acetylsalicylic acid, (5Z, 9α, 11α, 13E, 15S)-6,9-epoxy-11,15-dihydroxyprosta-5,13-dien-1-oic acid [1S-[1α,2β(Z), 3α(S*),5α]]-7-[3-(Cyclopentylhydroxy-acetal)amino]-6,6-dimethyl bicyclo[3.1.1]hept-2-yl]-5-heptenoic acid, [1α(Z),2β,5α]-(±)-7-[2-(4-Morpholinyl)-3-oxo-5-(phenyl-methoxy)cyclopentyl]-5-heptenoic acid methyl ester, [p-[2-(Benzene sulfonamido)ethyl]phenoxy] acetic acid, [p-[2-chlorobenzene sulfonamido)ethyl] phenoxy]-acetic acid, [1α,2α(Z), 3α(1E, 3S* ,4R*),4α]-7-[3-(3-Hydroxy)-4-phenyl-1-pentenyl)-7-oxabicyclo[2.2.1] hept-2-yl]-5-heptenoic acid and (+)-(Z)-7-[(1R,2R,3S,5S)-3-Hydroxy-5-[(p-phenylbenzyl)oxy]-2-piperidino cyclopentyl]-4-heptenoic acid.

14. The method of claim 9 wherein said calcium antagonist is selected from the group consisting of (E)-1]-Bis(4-fluorophenyl)methyl]-4-(3-phenyl-2propenyl)piperazine,4-[4,4-Bis(4-fluorophenyl)butyl]-N-(2,6-dimethylphenyl)-1-piperazine-acetamide, 1-(Diphenylmethyl)-4-(3-phenyl-2-propenyl)piperazine, Beta-[2-methylpropoxy)methyl]-N-phenyl-N-(phenylmethyl)-1-pyrrolidineethanamine, (±)-N-Dimethylphenyl)-4-[2-hydroxy-3-(2-methoxy phenoxy) propyl]-1-piperazineacetamide, gamma-phenyl-N-(1-phenylethyl)benzene-propanamine, 4-[4,4-Bis(p-fluoro phenyl)butyl]-3-carbamoyl-2',6'-dichloro-1-piperazine acetanilide, 1-[1-(Isobutoxymethyl)-2-[[1-(1-propynyl) cyclo-hexyl]oxy]ethyl]pyrrolidine, N-1,3-Benzodioxol-5yl-β[(2-methyl propoxy)methyl-N-(phenylmethyl)-1-pyrrolidine ethanamine, N-(2-Guanidinoethyl)-5-isoquinoline-sulfonamide, Hexahydro-1-(5-isoquinolinylsulfonyl)-1H-1,4-diazepine, 2-[3-[(3,4-dimethoxy phenethyl)methylamino]propyl]-5,6-dimethoxyphthalimidine, (−)-1,2,3,4-Tetrahydro-1-(3,4,5-trimethoxybenzyl)-6,7-isoquinolinediol, 3-[3-[(3,4-Dimethoxy phenethyl)methylamino]-propyl]-1,3,4,5-tetrahydro-7,8-dimethoxy-2H-3-benzazepin-2-one, 5-[N-(3, 4-Dimethoxy phenethyl)-β-alanyl]-2,3,4,5-tetrahydro-1,5-benzothiazepine.

15. A pharmaceutical composition suitable for the treatment and prevention of ischemia/reperfusion injury comprising:

(a) Thalidomide (b) One or more therapeutic agents selected from the groups consisting of nitrates, beta-adrenoceptor blocking agents, anti-platelet/thrombolytic drugs, drugs acting on the arachidonic acid cascade and calcium antagonists; and (c) A pharmaceutically-acceptable inert carrier.

16. The composition of claim 15 wherein said nitrate is selected from the group consisting of glyceryl trinitrate, isosorbide dinitrate and isosorbide 5 mononitrate.

17. The composition of claim 15 wherein said beta-adrenoceptor blocking agent is selected from the groups consisting of 2-hydroxy-5-[1-hydroxy-2-[(1 methyl-3 phenylpropyl amino]ethyl]benzamide, (±)-5-[2-[[3-(1,1-dimethylethyl)-amino]-2-hydroxypropyl]thio]-4-thiazolyl]-2thiophenecarboxamide, 1-(9H-carbozol-4-yloxy)-3-[[2-(2-methoxyphenoxy)ethyl]amino]-2 propanol, N'-[3 acetyl-4-[3-(1,1-dimethylethyl)-amino]-2-hydroxypropoxyl]phenyl]-N,N-diethylurea, [R-(R*R*)]-2 hydroxy-5-[1-hydroxy-2-[(1 methyl-3-phenylpropyl)amino]ethyl]benzamide, 3,4-dihydro -8-[2-hydroxy-3-(1-methylethyl)amino]-2H-1-benzopyran-3-ol 3 nitrate, (±)-1-[3,4-dihydro-2H-1-benzothio-pyran-8-yl)oxy]-3-(1,1-dimethylethyl)amino]-2-propanol.

18. The composition of claim 15 wherein said anti-platelet/thrombolytic drug is selected from the group consisting of of 5-[2-chlorophenyl)methyl]-4,5,6,7-tetrahydrothieno[3,2-c]pyridine, acetylsalicylic acid, streptococcal fibrinolysin, and fibrinokinase.

19. The composition of claim 15 wherein said drug acting on the arachidonic acid cascade is selected from the group consisting of 1-(4-chlorobenzoyl)-5-methoxy-2-methyl-1H-indole-3-acetic acid, acetylsalicylic acid, (5Z,9α,11α,13E,15S)-6,9-epoxy-11,15-dihydroxyprosta-5,13-dien-1-oic acid [1S-[1α,2β(Z), 3α(S*),5α[[-7-[3-(Cyclopentylhydroxy-acetal)amino]-6,6-dimethyl bicyclo [3.1.1]hept-2-yl]-5-heptenoic acid, [1α(Z),2β,5α]-(+)-7-[2-(4-Morpholinyl)-3-oxo-5-(phenylmethoxy)cyclopentyl]-5-heptenoic acid methyl ester, [p-[2-(Benze sulfonamido) ethyl]phenoxy]acetic acid, [p-[2-chlorobenzene sulfonamido)ethyl]phenoxy]-acetic acid, [1α,2α(Z),3α(1E, 3S* ,4R*),4α]-7-[3-(3-Hydroxy-4-phenyl-1-pentenyl)-7-oxabicyclo[2.2.1]hept-2-yl]-5-hepten-oic acid and (+)-(Z)-7-[(1R,2R ,3S,5S)-3-Hydroxy-5-[(p-phenylbenzyl)oxy]-2-piperidino cyclopentyl]-4-heptenoic acid.

20. The composition of claim 15 wherein said calcium antagonists are selected from the group consisting of 1,4-dihydropyridine, benzothiazepines, phenyalkylamines, (E)-1-Bis(4-fluorophenyl)methyl]-4-(3-phenyl-2 propenyl) piperazine, 4-[4,4-Bis(4-fluorophenyl)butyl]-N-(2,6-dimethylphenyl)-1-piperazineacetamide, 1-(Diphenylmethyl)-4-(3-phenyl-2-propenyl)piperazine, Beta-[2-methyl propxy)methyl]-N-phenyl-N-(phenylmethyl)-1-pyrrolidineethanamine,(±)-N-Dimethyl phenyl)-4-[2-hydroxy-3-(2-methoxyphenoxy)propyl]-1-piperazineacetamide, gamma-phenyl-N-(1-phenylethyl) benzene-propanamine, 4-[4,4-Bis(p-fluoro phenyl)butyl]-3-carbamoyl-2',6'-dichloro-1-piperazine acetanilide, 1-[1-(Isobutoxymethyl)-2-[[1-(1-propynyl)cyclo-hexyl]oxy] ethyl]pyrrolidine, N-1,3-Benzodioxol-5yl-β[(2-methyl propoxy)methyl-N-(phenylmethyl)-1-pyrrolidine ethanamine, N-(2-Guanidinoethyl)-5-iso quinolinesulfonamide, Hexahydro-1-(5-iso-quinolinylsulfonyl)-1H-1,4-diazepine, 2-[3-[(3,4-dimethoxy phenethyl) methylamino]propyl]-5,6-dimethoxyphthalimidine,(−)-1,2, 3,4-Tetrahydro-1-(3,4,5-trimethoxy-benzyl)-6,7-isoquinolinediol, 3-[3-[(3,4-Dimethoxy phenethyl) methylamino]-propyl]-1,3,4,5-tetrahydro-7,8-dimethoxy-2H-3-benazepin-2-one, 5-[N-(3,4-Dimethoxy phenethyl)-β-alanyl]-2,3,4,5-tetrahydro-1,5-benzothiazepine.

* * * * *